(12) United States Patent
Costello et al.

(10) Patent No.: US 10,939,846 B2
(45) Date of Patent: *Mar. 9, 2021

(54) ELONGATED CATHETER HAVING SENSOR AND AN EXTENDED WORKING CHANNEL

(71) Applicant: Covidien LP, Mansfield, MA (US)

(72) Inventors: David M. Costello, Delano, MN (US); Alex A. Peterson, Maple Grove, MN (US); Benjamin Greenburg, Hod Hasharon (IL); Thomas D. Magnuson, Philadelphia, PA (US); Brian T. Stolz, Bloomington, MN (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,940

(22) Filed: Mar. 2, 2020

(65) Prior Publication Data

US 2020/0196904 A1 Jun. 25, 2020

Related U.S. Application Data

(63) Continuation of application No. 15/228,321, filed on Aug. 4, 2016, now Pat. No. 10,575,754.

(Continued)

(51) Int. Cl.
*A61B 5/06* (2006.01)
*A61M 25/00* (2006.01)
(Continued)

(52) U.S. Cl.
CPC .............. *A61B 5/06* (2013.01); *A61B 1/2676* (2013.01); *A61B 5/061* (2013.01); *A61B 5/062* (2013.01);
(Continued)

(58) Field of Classification Search
CPC ........................................................ A61B 5/06
See application file for complete search history.

(56) References Cited

U.S. PATENT DOCUMENTS 5,386,828 A 2/1995 Owens et al.
5,727,553 A 3/1998 Saad
(Continued)

FOREIGN PATENT DOCUMENTS

CN 104840249 A 8/2015
CN 105615991 A 6/2016
(Continued)

OTHER PUBLICATIONS

European Search Report dated Mar. 2, 2017, issued in EP Application No. 16189889.

(Continued)

*Primary Examiner* — Lee S Cohen (57) ABSTRACT

A flexible catheter includes an elongated body, and a sensor. The elongated body has proximal and distal end portions and defines a working channel therethrough. The sensor is disposed in the distal end portion of the elongated body and is adapted for detecting the position of a distal end of the elongated body within the anatomy of a patient. The sensor is formed from a wire that forms a first layer of wraps about the distal end portion of the elongated body and that includes first and second leads that form a twisted pair proximal to the first layer of wraps. The twisted pair of the first and second leads extends to the proximal end portion of the elongated body.

20 Claims, 6 Drawing Sheets

Related U.S. Application Data (60) Provisional application No. 62/222,449, filed on Sep. 23, 2015.

(51) Int. Cl.
  *A61B 1/267* (2006.01)
  *A61B 90/10* (2016.01)
  *A61B 34/20* (2016.01)
  *A61M 25/01* (2006.01)

(52) U.S. Cl.
  CPC .......... *A61B 90/10* (2016.02); *A61M 25/005* (2013.01); *A61M 25/0012* (2013.01); *A61B 2034/2051* (2016.02); *A61M 2025/0166* (2013.01)

(56) References Cited

U.S. PATENT DOCUMENTS

| | | |
|---|---|---|
| 5,830,222 A | 11/1998 | Makower |
| 5,938,603 A | 8/1999 | Ponzi |
| 6,078,830 A | 6/2000 | Levin et al. |
| 6,213,995 B1 | 4/2001 | Steen et al. |
| 6,253,770 B1 | 7/2001 | Acker et al. |
| 6,503,353 B1 | 1/2003 | Peterson |
| 6,690,963 B2 | 2/2004 | Ben-Haim et al. |
| 6,869,431 B2 | 3/2005 | Maguire et al. |
| 7,386,339 B2 | 6/2008 | Strommer et al. |
| 7,668,583 B2 | 2/2010 | Fegert et al. |
| 7,927,271 B2 | 4/2011 | Dimitriou |
| 8,285,362 B2 | 10/2012 | Dietz et al. |
| 8,287,453 B2 | 10/2012 | Li et al. |
| 8,361,066 B2 | 1/2013 | Long et al. |
| 8,611,984 B2 | 12/2013 | Greenburg et al. |
| 8,857,304 B2 | 10/2014 | Govari et al. |
| 9,078,570 B2 | 7/2015 | Parks et al. |
| 9,125,578 B2 | 9/2015 | Grunwald |
| 9,144,458 B2 | 9/2015 | Takaoka et al. |
| 10,575,754 B2 | 3/2020 | Costello et al. |
| 2005/0015044 A1 | 1/2005 | Harttig et al. |
| 2006/0287700 A1 | 12/2006 | White et al. |
| 2009/0018566 A1 | 1/2009 | Escudero et al. |
| 2009/0234328 A1 | 9/2009 | Cox et al. |
| 2010/0331644 A1 | 12/2010 | Neale et al. |
| 2011/0066029 A1 | 3/2011 | Lyu et al. |
| 2012/0149967 A1 | 6/2012 | Ludwin et al. |
| 2012/0172842 A1 | 7/2012 | Sela et al. |
| 2012/0265102 A1 | 10/2012 | Leo et al. |
| 2013/0169272 A1 | 7/2013 | Eichler |
| 2013/0245433 A1 | 9/2013 | Deladi |
| 2015/0080858 A1 | 3/2015 | Moss |
| 2015/0374435 A1 | 12/2015 | Cao et al. |
| 2016/0184013 A1 | 6/2016 | Brannan et al. |

FOREIGN PATENT DOCUMENTS

| | | |
|---|---|---|
| EP | 0421650 A1 | 4/1991 |
| WO | 2015160064 A1 | 10/2015 |

OTHER PUBLICATIONS

European Examination Report issued in corresponding Appl. No. EP 16189889.5 dated Feb. 14, 2019 (5 pages).

ELONGATED CATHETER HAVING SENSOR AND AN EXTENDED WORKING CHANNEL

CROSS-REFERENCE TO RELATED APPLICATIONS

This application is a continuation application of U.S. Pat. No. 10,575,754, filed on Aug. 4, 2016, which claims the benefit of, and priority to, U.S. Provisional Patent Application No. 62/222,449, filed on Sep. 23, 2015, the entire contents of which are hereby incorporated by reference.

FIELD

The present disclosure relates to elongated catheters and, more specifically, to methods of manufacturing elongated catheters including a sensor and an extended working channel.

BACKGROUND

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to placement (e.g., guide wires), diagnostic (e.g., biopsy tools) and therapeutic (e.g., treatment catheters or laser, cryogenic, radio frequency, or microwave tissue treatment probes) instruments.

During particular procedures (e.g., microwave ablation and biopsy) a catheter having an extended working channel may be inserted through a working channel to enable navigation to sites too remote and having luminal diameters too small for the bronchoscope. Generally, a locatable guide is positioned at a distal end of the extended working channel to guide the catheter to targeted tissue. When the distal end of the extended working channel is positioned adjacent targeted tissue, the locatable guide is removed from the extended working channel. Then, an instrument may be inserted through the extended working channel in order to act on the targeted tissue (e.g., perform a biopsy or ablation of the targeted tissue).

There is a need for a catheter having an extended working channel that includes a sensor for locating a distal end of the catheter within the anatomy of a patient with the extended working channel open for insertion of an instrument.

SUMMARY

In an aspect of the present disclosure, a flexible catheter includes an elongated body, and a sensor. The elongated body has proximal and distal end portions and defines a working channel therethrough. The sensor is disposed in the distal end portion of the elongated body and is adapted for detecting the position of a distal end of the elongated body within the anatomy of a patient. The sensor is formed from a wire that forms a first layer of wraps about the distal end portion of the elongated body and that includes first and second leads that form a twisted pair proximal to the first layer of wraps. The twisted pair of the first and second leads extends to the proximal end portion of the elongated body. The wire may be continuous from the first lead, through the first layer of wraps, and to the second lead.

In aspects, the elongated body includes a braid that defines the working channel and an outer coating that is disposed over the braid for isolating the working channel from an environment that surrounds the flexible catheter. The braid may be formed of cords that define channels therebetween. The twisted pair of the wire is disposed within one of the channels of the braid between the first layer of wraps and the proximal end portion of the elongated body. The elongated body may include an inner liner that is disposed within the braid. The outer coating may be bonded to the braid and may be formed from a reflowed polymer tube. The wire may be disposed within the outer coating between the distal and proximal end portions of the elongated body.

In some aspects, the first layer of wraps is transverse to a longitudinal axis of the elongated body. The wire may also form a second layer of wraps about the distal end portion over the first layer of wraps. The first layer of wraps may be in a first direction about the braid and the second layer of wraps is in a second direction about the distal end portion opposite the first direction.

In another aspect of the present disclosure, a catheter system includes a flexible catheter and a handle. The flexible catheter includes an elongated body that has proximal and distal end portions and defines a working channel therethrough. The sensor is disposed in the distal end portion of the elongated body and is adapted for detecting the position of a distal end of the elongated body within the anatomy of a patient. The sensor is formed from a wire has a first layer of wraps about the distal end portion. The wire including first and second leads that form a twisted pair proximal to the first layer of wraps and that extends to a proximal end portion of the elongated body. The handle is disposed over the proximal end portion of the elongated body. The handle is longitudinally and rotatably fixed to the flexible catheter. The handle includes an adapter that is in electrical communication with the sensor.

In aspects, the catheter system includes a telescopic channel that is disposed over a portion of the elongated body and that is coupled to a distal end of the handle.

In another aspect of the present disclosure, a method of manufacturing a flexible catheter includes wrapping a wire about a distal end portion of a braid, positioning first and second leads of the wire in a channel defined about the braid between the first layer of wraps and the proximal end portion of the braid, and forming an outer coating over the braid and the wire from a distal end of the braid to a proximal end portion of the braid. Wrapping the wire about the distal end portion of the braid forms a first layer of wraps transverse to a longitudinal axis defined by the braid. The wire may be continuous from the first lead, through the first layer of wraps, and to the second lead.

In aspects the method includes twisting the first and second leads together to form a twisted pair. Positioning the first and second leads in the channel may include positioning the twisted pair in the channel. Twisting and positioning the first and second leads may occur simultaneously.

In some aspects, forming the outer coating includes reflowing a distal polymer tube that is disposed over the braid and the wire from the distal end of the braid to the proximal end portion of the braid. Forming the outer coating may include reflowing a proximal polymer tube that is disposed over the proximal end portion of the braid proximal of the wire before reflowing the distal polymer tube. Forming the outer coating may include positioning an outer sleeve over the reflowed proximal polymer tube and wrapping the wire over the outer sleeve before reflowing the distal polymer tube. Reflowing the distal polymer tube may include reflowing the distal polymer tube into a portion of the reflowed proximal polymer tube over the wire.

In particular aspects, the method may include positioning an inner liner over a mandrel and forming a braid over the inner liner and the mandrel before wrapping the wire. Forming the braid over the braid may include weaving cords to form the braid. Forming the outer coating may include reflowing a distal polymer tube and the inner liner together from the distal end of the braid to the proximal end portion of the braid. The distal polymer tube may be disposed over the braid and the wire.

In certain aspects, the method of manufacturing includes trimming the braid after forming the outer coating. Trimming the braid may include cutting the distal end portion of the braid distal to the layer of wraps of the wire and cutting the proximal end portion of the braid.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

This disclosure relates generally to a catheter having an Extended Working Channel (EWC) and a sensor positioned at a distal end of the EWC for locating the distal end of the EWC within the anatomy of a patient. Such a catheter eliminates the need for a separate locatable guide to be inserted through the EWC to locate the distal end of the catheter within the anatomy of a patient. In addition, such a catheter eliminates the need to remove the locatable guide before insertion of an instrument through the EWC to treat targeted tissue. Further, such a catheter is locatable during an entire procedure such that the changes in the location of the distal end of the catheter are detectable and/or the catheter is repositionable during the procedure when an instrument positioned within the EWC.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figures 1, 2, 3:
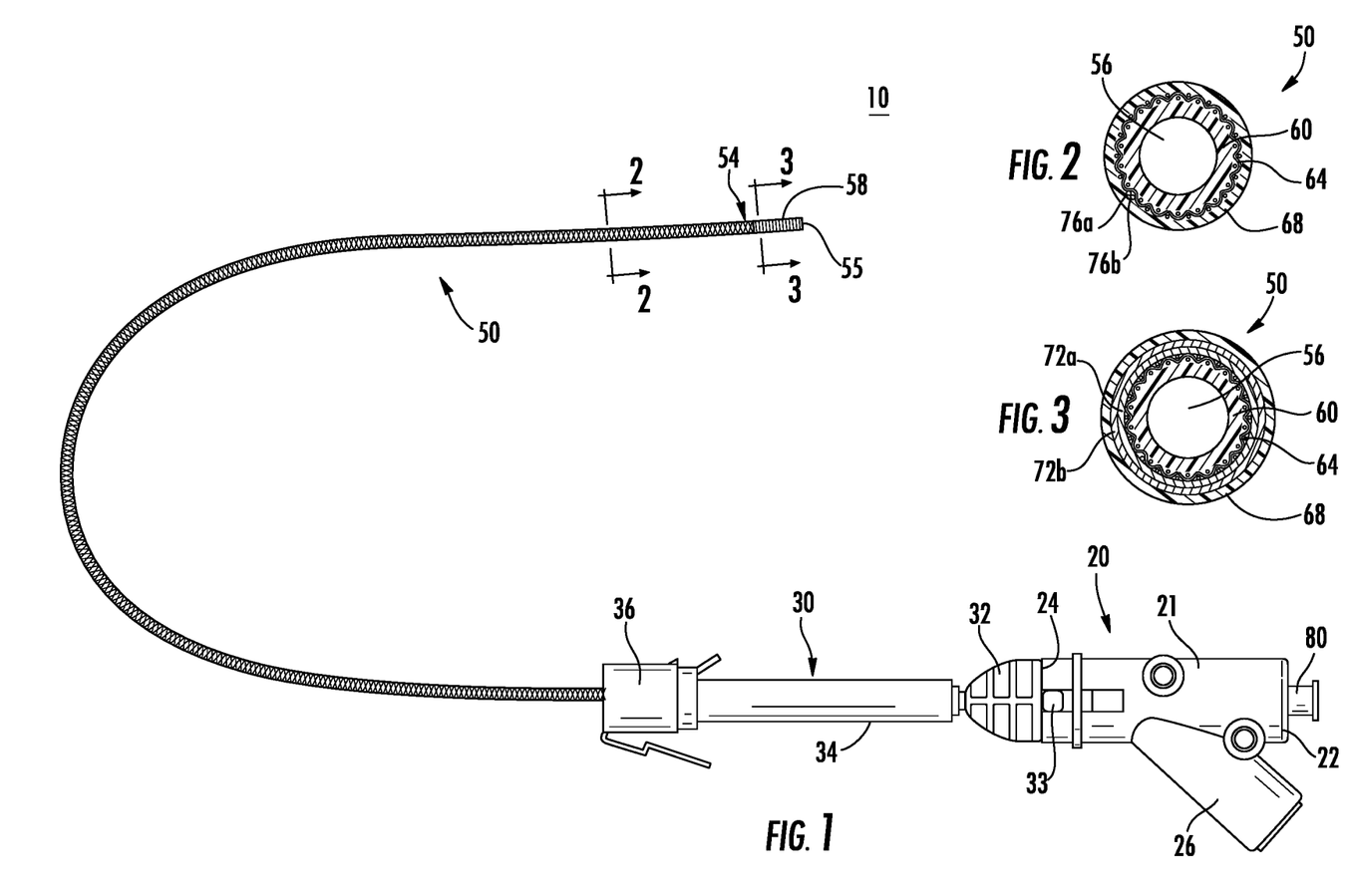
FIG. 1 is a side view of a catheter assembly provided in accordance with the present disclosure.
FIG. 2 is a cross-sectional view of the catheter assembly of FIG. 1 taken along the section line 2-2 of FIG. 1.
FIG. 3 is a cross-section view of the catheter assembly of FIG. 1 taken along the section line 3-3 of FIG. 1.
Figure 4:
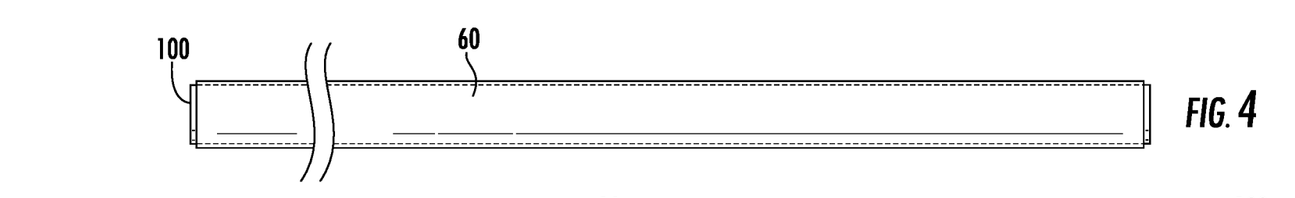
FIG. 4 is a side view of an inner liner of the catheter assembly of FIG. 1 over a mandrel.

Referring now to FIG. 1, a catheter assembly 10 is provided in accordance with the present disclosure and includes a handle assembly 20, a telescopic channel 30, and an elongated catheter 50 having a proximal end portion 52 (FIG. 12) and a distal end portion 54. The handle assembly 20 is positioned over the proximal end portion 52 of the catheter 50 to permit a clinician to manipulate the catheter assembly 10. The telescopic channel 30 is positioned over the catheter 50 between the proximal end portion 52 and the distal end portion 54 to provide lateral support for the elongated catheter 50. The telescopic channel 30 includes a proximal or first end 32 that is coupled to a distal end 24 of the handle assembly 20 and a distal or second end 36 that is configured to couple the catheter assembly 10 to a bronchoscope (not shown). The telescopic channel 30 includes an extendable body portion 34 between the first and second ends 32, 36 that is expandable along a longitudinal axis and substantially rigid transverse to the longitudinal axis. The extendable body portion 34 allows the first end 32 to translate along and rotate about the longitudinal axis relative to the second end 36. When the first end 32 is coupled to the handle assembly 20, the proximal end portion 52 of the catheter 50 translates and rotates with the first end 32 of the telescopic channel 30.

Examples of methods of marking the location of and registering a pathway to targeted tissue may be found in commonly assigned U.S. Provisional Patent Application Nos. 62/020,177, filed Jul. 2, 2014, entitled "Methods for Marking Biopsy Location," and 62/020,220, filed Jul. 2, 2014, entitled "Real-time Automatic Registration Feedback." Examples of guiding a catheter to and treating targeted tissue may be found in commonly assigned U.S. Patent Publication Nos. 2014/0281961 and 2014/0046315. Examples of bronchoscopes, handles, and support systems for microwave ablation catheters may be found in commonly assigned U.S. Patent Publication No. 2015/0073407. The entire contents of each of these disclosures are incorporated herein by reference.

With additional reference to FIGS. 2 and 3, the catheter 50 has a proximal end 53 (FIG. 13) and a distal end 55 and defines an EWC 56 therebetween. The EWC 56 allows instruments (not shown) to be inserted through the catheter 50 to treat targeted tissue adjacent the distal end 55 of the catheter 50. The catheter 50 includes a sensor 58 disposed at the distal end portion 54 of the catheter 50 adjacent the distal end 55 of the catheter 50 such that the distal end 55 of the catheter 50 is locatable within the anatomy of a patient.

With particular reference to FIGS. 2 and 3, the catheter 50 includes an inner liner 60, a braid 64, and an outer coating 68. The inner liner 60 defines the EWC 56 that passes entirely through the catheter 50. It is contemplated that the catheter 50 may be constructed without the inner liner 60 such that the braid 64 defines the EWC 56. As described in greater detail below, the sensor 58 is formed of a wire 71 (FIG. 5) wrapped over the braid 64 and covered by the outer coating 68 to form the sensor 58. The wire 71 includes leads 76a, 76b that proximally follow the braid 64 to the proximal end portion 52 (FIG. 12) of the catheter 50. It will be appreciated that while the portions of the wire 71 (e.g., the sensor 58 and the leads 76a, 76b) are discussed individually herein, that the wire 71 is monolithically formed (i.e., the wire 71 is a continuous wire without any solder joints between different portions thereof). By forming the sensor 58 and the leads 76a, 76b from a continuous monolithic wire, the useful life of the sensor 58, and thus the catheter 50, is increased.

The inner liner 60 and the outer coating 68 are formed from polymer tubes, as detailed below, which are made from of a reflowable polymer material (e.g., Arnitel®, Hytrel®, Pebax®, polytetrafluoroethylene (PTFE)) which may bond to the braid 64, the wire 71, and to one another. The braid 64 is constructed of a mesh of between 16 and 32 of similar or varying material cords woven together (e.g., stainless steel, Dacron®, polyethylene naphthalate (PEN), polyethylene terephthalate (PET), and/or insulated electrical wire). The wire 71 is a solid core magnetic wire with a thin dielectric coating (e.g., a copper wire with a polyimide coating).

Referring now to FIGS. 4-15, the construction of the catheter 50 and a method of manufacturing the catheter assembly 10 will be described in accordance with the present disclosure. Initially referring to FIG. 4, the inner liner 60 is slid over a mandrel 100. The mandrel 100 provides rigidity to the flexible components of the catheter 50 while the catheter 50 is assembled. The inner liner 60 has an inner diameter substantially equal to but slightly larger than an outer diameter of the mandrel 100 and has a length substantially equal to a length of the mandrel 100. The mandrel 100 may be coated with a PTFE coating to assist in sliding the inner liner 60 over the mandrel 100 and to prevent the inner liner 60 from bonding to the mandrel 100. The outer diameter of the mandrel 100 is substantially equal to a desired diameter of the EWC 56 (FIG. 2) and the length of the mandrel 100 is longer than a final desired length of the catheter 50. The mandrel 100 may have a diameter in a range of about 0.050 to about 0.100 inches (e.g., about 0.090 inches) and have a length in a range of about 30 to about 90 inches (e.g., about 62 inches).

Figure 5:
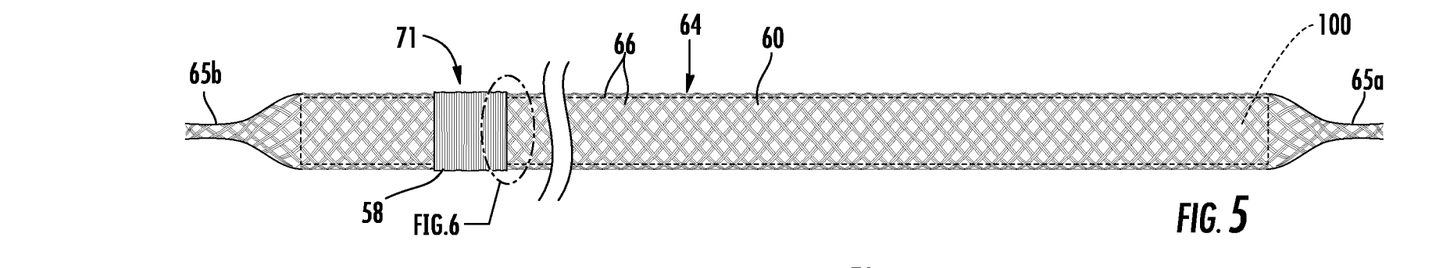
FIG. 5 is a side view of a braid over the inner liner of FIG. 4.

With particular reference to FIG. 5, the braid 64 is formed over the inner liner 60 with portions of the braid 64 extending beyond the ends of the mandrel 100 such that the mandrel 100 and the inner liner 60 are completely within the braid 64. The ends 65a, 65b of the braid 64 that extend beyond the mandrel 100 may have a diameter less than the diameter of the mandrel 100. By having a diameter less than the mandrel 100, the ends 65a, 65b of the braid 64 may retain the mandrel 100 within the braid 64 during construction of the catheter 50. It is contemplated that the braid 64 may be preformed and slid over the inner liner 60 and the mandrel 100.

The braid 64 is formed by helically weaving cords 66 of material over a cylinder (e.g., the inner liner 60 and the mandrel 100. The cords 66 define channels 67 therebetween that follow the helical pattern of the cords 66. The pitch of the cords 66 is in a range of about 0.125 to about 0.225 (e.g., about 0.177). The braid 64 may compress the inner liner 60 over the mandrel 100. The braid 64 has an outer diameter in a range of about 0.052 to about 0.102 inches (e.g., 0.092 inches). It is contemplated that the inner liner 60, the braid 64, and the mandrel 100 may be supplied as a preassembled unit.

Figure 6:
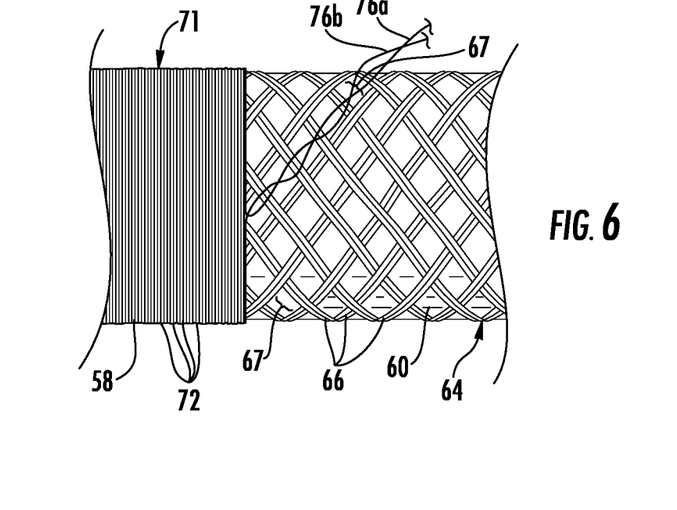
FIG. 6 is an enlarged view of the area of detail of FIG. 5.

With reference to FIGS. 5 and 6, the sensor 58 is formed by wrapping the wire 71 over the braid 64, or over the mandrel 100 and inner liner 60 just distal to the braid termination, transverse to a longitudinal axis of the braid to form wraps 72 over the braid 64, or over the mandrel 100 and inner liner 60. Referring briefly back to FIG. 3, the wraps 72 may include an inner layer 72a and an outer layer 72b of wraps 72. Each layer of wraps 72a, 72b may include a range of about 25 to about 200 individual wraps 72 (e.g., about 100 individual wraps) of the wire 71. The number of wraps 72 in the inner layer 72a may be substantially equal to the number of wraps 72 of the outer layer 72b.

As shown, the sensor 58 includes two layers of wraps 72a, 72b; however, it is contemplated that the sensor 58 may include a single layer of wraps 72 or may include more than two layers of wraps 72. The number of wraps 72 of the wire 71 is proportional to signal strength of the sensor 58. That is, as the number of wraps 72 increases, the signal strength of the sensor 58 increases. As the number of layers of wraps 72 is increased, the flexibility of the catheter 50 in the area of the wraps 72 is reduced and the diameter of the catheter 50 in the area of the wraps 72 is increased.

The total length of the layers 72a, 72b of the wraps 72 is in a range of about 0.04 to about 0.36 inches (e.g., about 0.18 inches). As the total length of the layers 72a, 72b is increased, the flexibility of the catheter 50 in the area of the wraps 72 is reduced. Thus, the number of layers of wraps 72, the length of the wraps 72, and the total number of wraps 72 is a compromise between the signal strength of the sensor 58 and the flexibility and size of the catheter 50.

The wraps 72 are formed by ends or leads 76a, 76b of the wire 71 being wrapped around about the braid 64. The inner and outer layers 72a, 72b may be formed simultaneously by beginning at a distance spaced away from a distal end 65b of the braid 64. The inner layer 72a is formed by a first lead 76a being wrapped around the braid 64 in a first direction substantially transverse to a longitudinal axis of the braid 64 while proximally traversing an outer surface of the braid 64. The outer layer 72b is formed by a second lead 76b being wrapped around the braid 64 and the inner layer 72a in a second direction, opposite to the first direction, substantially transverse to a longitudinal axis of the braid 64 while proximally traversing the inner layer 72a. The wrapping of the second lead 76b trails the wrapping of the first lead 76a in a range of about 1 to about 5 wraps 72 of the wire 71 (e.g., 2 wraps) to allow the inner layer 72a to form before being covered by the outer layer 72b. The wraps 72 are started spaced away from the distal end 65b of the braid 64 a distance in a range of about 0.0 to about 3.0 inches (e.g., about 0.5 inches). The wraps 72 are spaced away a distance from the distal end 65b of the braid 64 large enough to ensure that the inner liner 60 and the braid 64 are substantially cylindrical in shape in the region of the wraps 72 while minimizing the distance the wraps 72 are space away from the distal end 65b to reduce wasted materials.

In embodiments where the sensor 58 includes an odd number of wraps 72, one lead exits the sensor 58 at a proximal end of the sensor 58 and the other lead exits the sensor at a distal end of the sensor 58. The lead that exits the sensor 58 at the distal end is placed under or over the wraps 72 prior to wrapping the leads 76a, 76b over the braid 64 as detailed below.

Additionally, a support tube or layer may be positioned over the braid 64 before the wire 71 is wrapped over the braid 64 to form the sensor 58 or may be placed over the sensor 58 after the wire 71 is wrapped over the braid to form the sensor 58. The support layer may be a ferro-metallic tube or a powder with resin that is configured to strengthen or support the sensor 58 to prevent the sensor 58 from deforming when used. The support layer may increase the signal strength of the sensor 58 such that the length and/or number of wraps 72 required to achieve a desired signal strength for the sensor 58 may be reduced.

Figure 7:
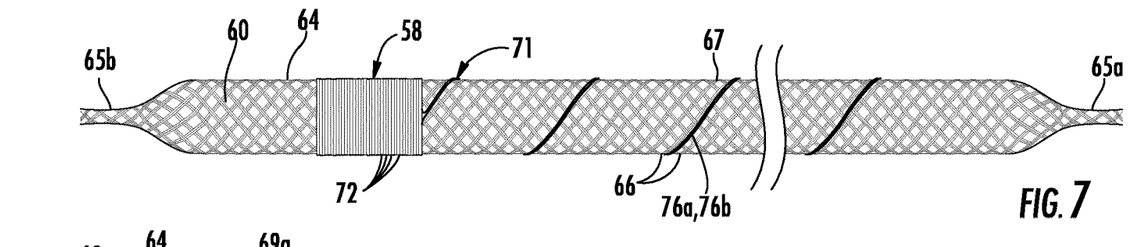
FIG. 7 is a side view of a wire wrapped over the braid of FIG. 5 towards a proximal end of the braid.

With particular reference to FIG. 6, the leads 76a, 76b are brought together within a channel 67 defined between two cords 66 of the braid 64 at a proximal end of the wraps 72. The leads 76a, 76b of the wire 71 are twisted together to form a twisted pair to reduce or eliminate a signal from being generated by the wire 71 along the length of the braid 64 (i.e., utilizing the constructive interference to minimize the signal generated). The leads 76a, 76b are twisted together in a range of about 5 to about 15 twists per inch (e.g., about 10 twists per inch) of the wire 71. The twisted pair of leads 76a, 76b is wrapped around the braid 64 within a channel 67 of the braid 64 such that the twisted pair of leads 76a, 76b follows the pitch of the braid 64 as shown in FIG. 7. Wrapping the twisted pair of leads 76a, 76b helically around the braid 64 may increase the fatigue life of the leads 76a, 76b in response to flexing of the catheter 50 along its longitudinal axis. The twisted pair of leads 76a, 76b is wrapped about the braid 64 from the wraps 72 along a substantial length of the braid 64 towards a proximal end 65a of the braid 64. As shown, the twisted pair of leads 76a, 76b are wrapped about the braid 64 in a clockwise direction when viewed from the proximal end 65a of the braid 64; however, the twisted pair of leads 76a, 76b may be wrapped about the braid 64 in a counter-clockwise direction when viewed from the proximal end 65a of the braid 64. By forming the wraps 72 and the twisted pair of leads 76a, 76b with a single continuous wire increases the service life of the catheter 50 by eliminating the need for a connection (e.g., a soldered connection) between the wraps 72 and each of the twisted pair of leads 76a, 76b.

It is contemplated that a single device or a combination of devices may be used to wrap the wire 71 about the braid 64 to form the wraps 72, twist the pair of leads 76a, 76b of the wire 71 together, and wrap the twisted pair of leads 76a, 76b of the wire 71 about the braid 64. Alternatively, it is contemplated that the wraps 72 and the twisted pair of leads 76a, 76b may be preformed apart from the braid and then positioned or loaded over the braid 64. Once the wraps 72 are loaded over the braid 64, the twisted pair of leads 76a, 76b are wrapped about the braid 64 as detailed above.

Figure 8:
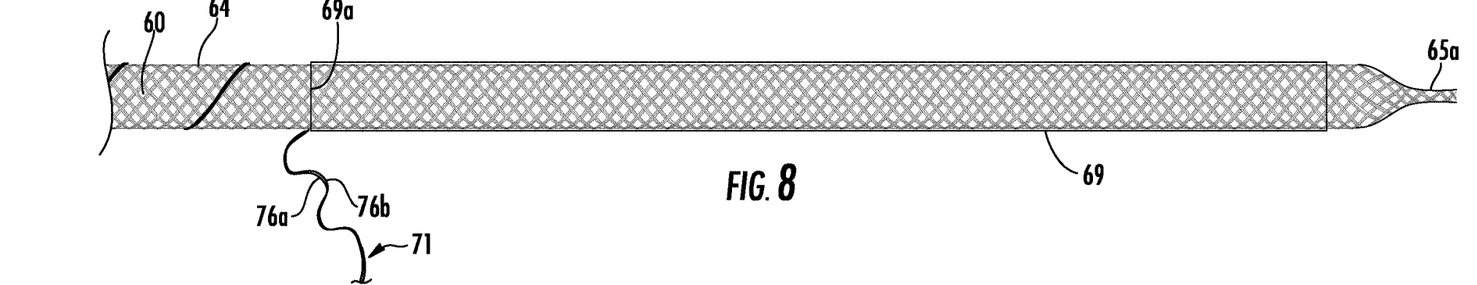
FIG. 8 is a side view of a first outer tube slid over a proximal end of the braid of FIG. 7.

Referring now to FIG. 8, with the twisted pair of leads 76a, 76b wrapped about the braid 64, a first outer tube 69 is slid over the proximal end 65a of the braid 64 until a proximal end 69a of the first outer tube 69 is adjacent to the twisted pair of leads 76a, 76b. The first outer tube 69 is a polymer tube which is then covered by heat shrink to melt or reflow the polymer such that the first outer tube 69 reflows or bonds to the braid 64. In addition, when the first outer tube 69 is reflowed, the inner liner 60 within the first outer tube 69 may be reflowed to bond with the braid 64 and the first outer tube 69. The outer diameter of the first outer tube 69 may be slightly reduced as the first outer tube 69 is reflowed.

Figure 9:
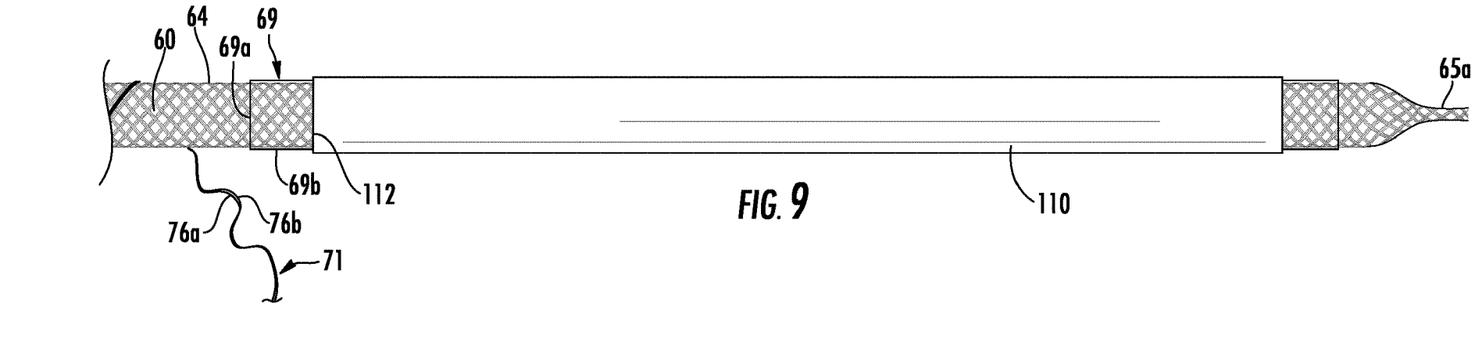
FIG. 9 is a side view of an outer sleeve positioned over the first outer tube of FIG. 8.
Figure 10:
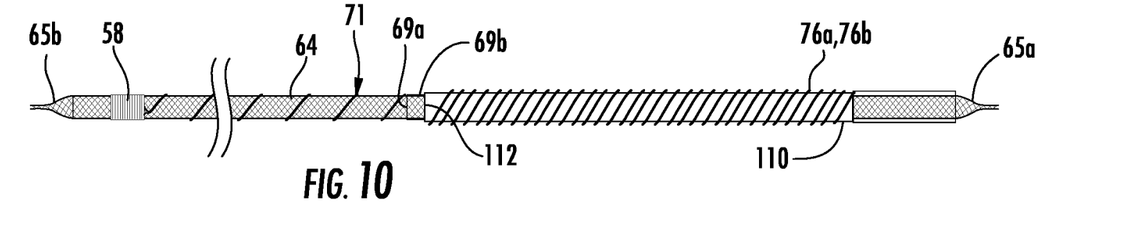
FIG. 10 is a side view of the wire wrapped over a portion of the first outer tube and the outer sleeve of FIG. 9.

With reference to FIG. 9, an outer sleeve 110 is slid over the reflowed first outer tube 69 until a distal end 112 of the outer sleeve 110 is adjacent a distal end 69a of the first outer tube 69. A portion 69b of the first outer tube 69 is exposed between the twisted pair of leads 76a, 76b and the outer sleeve 110. The twisted pair of leads 76a, 76b is then wrapped over the exposed portion 69b of the reflowed first outer tube 69 and over the outer sleeve 110 as shown in FIG. 10. The outer sleeve 110 is constructed of or lined with PTFE such that the outer sleeve 110 and the leads 76a, 76b are prevented from bonding to a portion of the reflowed first outer tube 69 covered by the outer sleeve 110.

Figure 11:
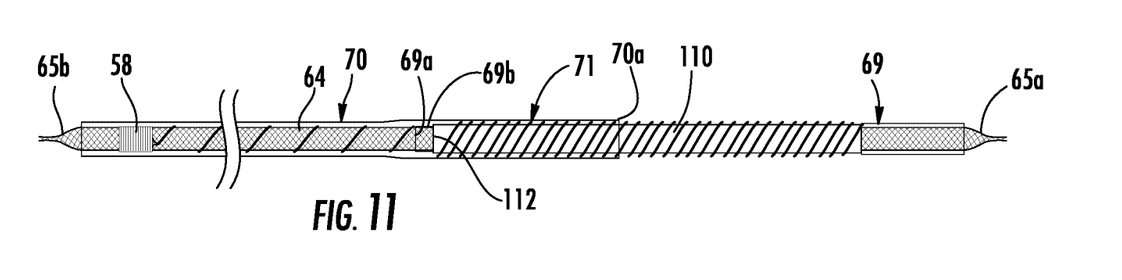
FIG. 11 is a side view of a second outer tube slid over a distal end of the braid, a portion of the wire, a portion of the first outer tube, and a portion of the outer sleeve of FIG. 10.

Referring to FIG. 11, a second outer tube 70 is slid over the distal end 65b of the braid 64, the sensor 58, the twisted pair of leads 76a, 76b, the exposed portion 69b of the first outer tube 69, and a portion of the outer sleeve 110. Similar to the first outer tube 69, the second outer tube 70 has an inner diameter slightly larger than the braid 64 such that the second outer tube 70 freely slides over the braid 64, the wire 71, the reflowed first outer tube 64, and the outer sleeve 110. A proximal end 70a of the second outer tube 70 is positioned along the outer sleeve 110. The second outer tube 70 is a polymer tube which is then covered by heat shrink to reflow the polymer such that the second outer tube 70 bonds to the braid 64 and to the exposed portion 69b of the first outer tube 69. In addition, when the second outer tube 70 is reflowed, the inner liner 60 and the first inner tube 69 within the second outer tube 70 may be reflowed to bond with the braid 64, the second outer tube 70, and the wire 71. After the second outer tube 70 is reflowed, the first and second outer tubes 69, 70 form the outer coating 68 as a continuous layer of polymer over the braid 64 and a substantial portion of the wire 71. The outer coating 68 is substantially smooth and seals the EWC 64 (FIG. 3). As shown, the outer coating 68 is translucent or transparent; however, the outer coating 68 may be opaque and have a desired color (e.g., blue or white).

Figure 12:
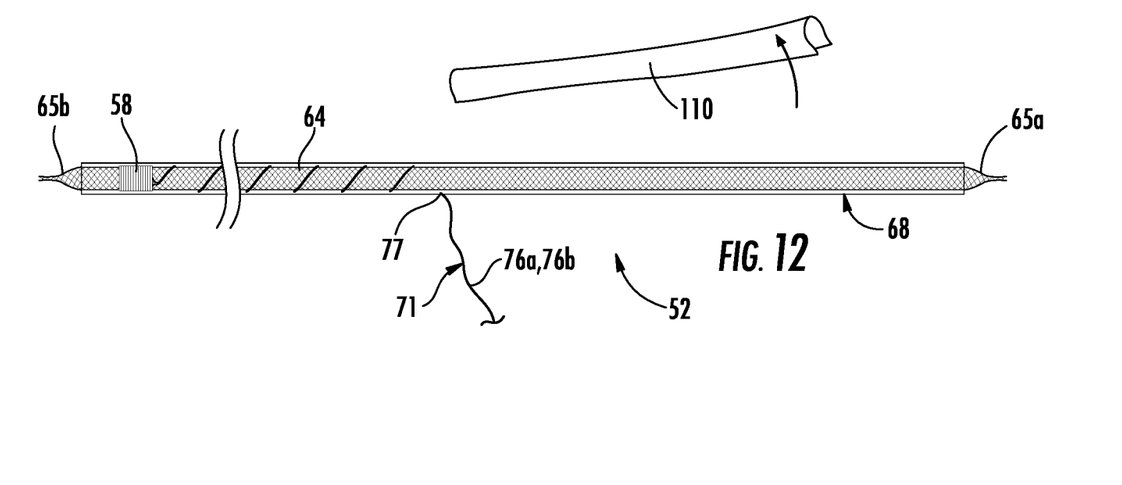
FIG. 12 is a side view of an outer coating formed over the braid from the first and second outer tubes with the wire unwrapped from over the outer sleeve and the outer sleeve removed from over the first outer tube of FIG. 11.

With particular reference to FIG. 12, with the outer coating 68 formed, the twisted pair of leads 76a, 76b is unwrapped from over the outer sleeve 110 in a manner not to damage the leads 76a, 76b. Then the outer sleeve 110 is peeled off or removed from over the portion of the outer coating 68 previously formed from first outer tube 69. Any portion of the second outer tube 70 that is formed over the outer sleeve 110 is separated from the outer coating 68 and discarded.

Figure 13:
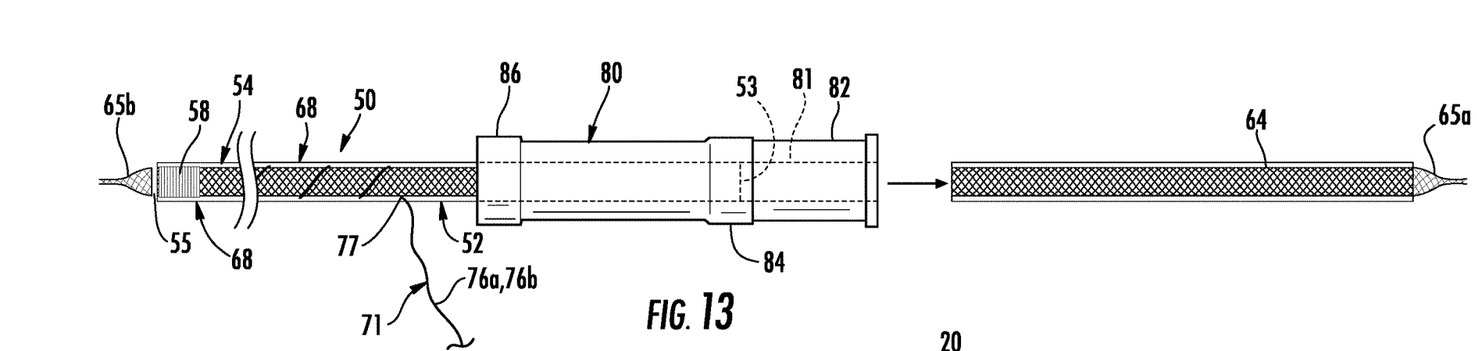
FIG. 13 is a side view of the catheter of FIG. 1 being cut to length from the braid, wire, and outer coating of FIG. 12.

Referring to FIG. 13, the catheter 50 is cut adjacent the proximal end 65a of the braid 64 to define a proximal end 53 of the catheter 50. The catheter 50 is cut a distance spaced away from a point 77 where the leads 76a, 76b pass through the outer coating 68 to leave a proximal end portion 52 of the catheter 50 where the leads 76a, 76b are not wrapped around the braid 64. The catheter 50 is also cut adjacent the sensor 58 to define the distal end 55 of the catheter 50. The cut adjacent the sensor 58 is spaced apart a minimal distance from the sensor 58 to prevent discontinuities in the wire 71 forming the sensor 58; however, this distance is minimized to allow the sensor 58 to be positioned as close to the distal end 55 of the catheter as possible. The distal end 55 of the catheter 50 may be reflowed to seal the portions of the braid 64 exposed by cutting adjacent the sensor. Additionally or alternatively, a catheter tip (not shown) may also be bonded to the distal end 55 of the catheter 50. After the catheter 50 is cut, the catheter 50 has a total length of about 30 to about 90 inches (e.g., about 60 inches) from the proximal end 53 to the distal end 55.

Still referring to FIG. 13, after the catheter 50 is cut to length, a hub 80 is positioned over the proximal end portion 52 of the catheter 50. The hub 80 defines a channel 81 therethrough and includes a proximal guide portion 82, a central collar 84, and a distal collar 86. The proximal end portion 52 of the catheter 50 is positioned within the channel 81 of the hub 80 such that the proximal end 53 of the catheter is adjacent the central collar 84 of the hub 80. The hub 80 is then bonded to the proximal end portion 52 of the catheter 50. The hub 80 may be reflowed into the outer coating 68 of the catheter 50 or bonded to the outer coating 68 using adhesives. The proximal guide portion 82 is configured to guide an instrument (not shown) into the EWC (FIG. 3) of the catheter 50.

Figure 14:
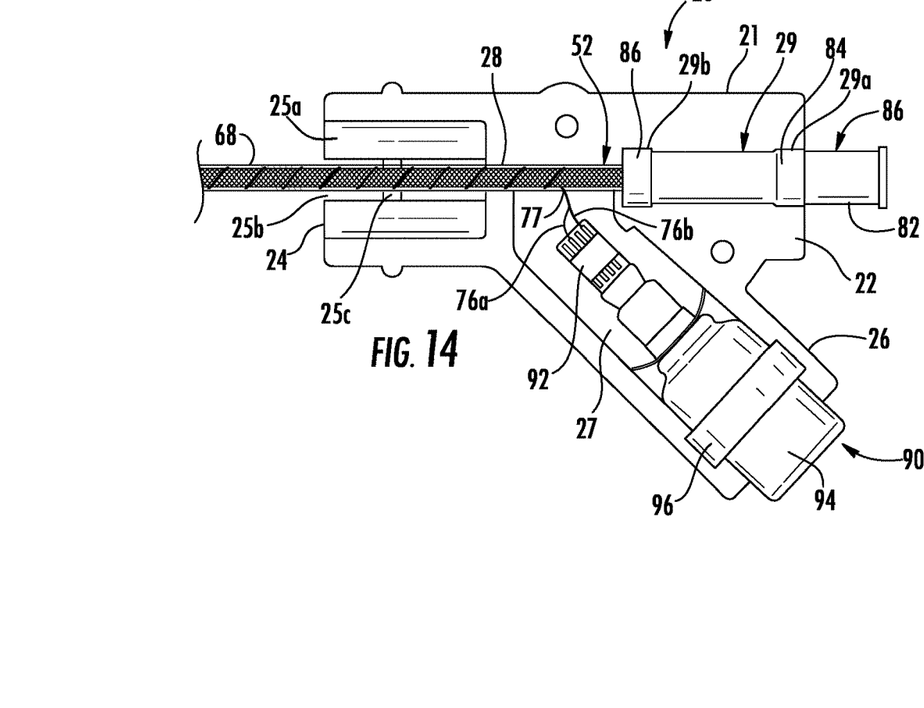
FIG. 14 is a side view of a proximal end portion of the catheter of FIG. 13 positioned in a body of a handle assembly with a half-shell of the body removed.

With particular reference to FIG. 14, the handle assembly 20 is coupled over the proximal end portion 52 of the catheter 50. The handle assembly 20 includes a body 21 formed from two half shells coupled together over the proximal end portion 52 of the catheter 50. Each of the half shells of the body 21 is substantially similar to one another and is joined along the longitudinal axis of the catheter 50. The body 21 has a proximal end 22, a distal end 24, and a connector portion 26. The body 21 defines a catheter passage 28 that is configured to receive the catheter 50 with the hub 80 bonded to the distal end 52. The catheter passage 28 includes an enlarged proximal portion 29 including a first recess 29a and a second recess 29b. The proximal portion 29 is sized to receive the hub 80 to longitudinally fix the catheter 50 relative to the handle 20. The first recess 29a is sized to receive the central collar 84 of the hub 80 and the second recess 29b is sized to receive the distal collar 86 of the hub 80. The proximal portion 29 of the catheter passage 28 between the first and second recesses 29a, 29b has a diameter smaller than the first and second recesses 29a, 29b to fix the hub 80 within the catheter passage 28. The hub 80 is frictionally engaged with the body 21 to rotatably secure the hub 80 within the catheter passage 28. It is contemplated that the hub 80 may be adhered to the body 21 within the catheter passage 28.

With continued reference to FIG. 14, the handle 20 includes an electrical coupling 90 disposed within a cavity 27 of the connector portion 26 of the handle 20. The electrical coupling 90 includes an internal connector 92, an external connector 94, and a collar 96 positioned between the internal and external connectors 92, 94. The collar 96 is received by the connector portion 26 of the handle 20 to form a seal to isolate the internal connector 92 within the cavity 27 of the connector portion 26. The cavity 27 of the connector portion 26 is isolated from the external environment by a seal formed by the walls defining the catheter passage 28 engaging the outer coating 68 of the catheter 50 and the seal formed by the collar 96 engaging walls defining the cavity 27 of the connector portion 26.

The point 77 at which the twisted pair of the leads 76a, 76b exits through the outer coating 68 of the catheter 50 is positioned within the cavity 27 of the connector portion 26. The leads 76a, 76b are untwisted from one another and electrically coupled (e.g., soldered) separately to the internal connector 92. The internal connector 92 is in electrical communication with the external connector 94 such that an adapter (not shown) may be coupled to the external connector 94 to supply electrical energy to the sensor 58 (FIG. 1) through the external connector 94 via the wire 71. Examples of systems and methods for using the sensor 58 to guiding the catheter 50 to targeted tissue may be found in commonly assigned U.S. Patent Publication Nos. 2014/0281961 and 2014/0046315.

Figure 15:
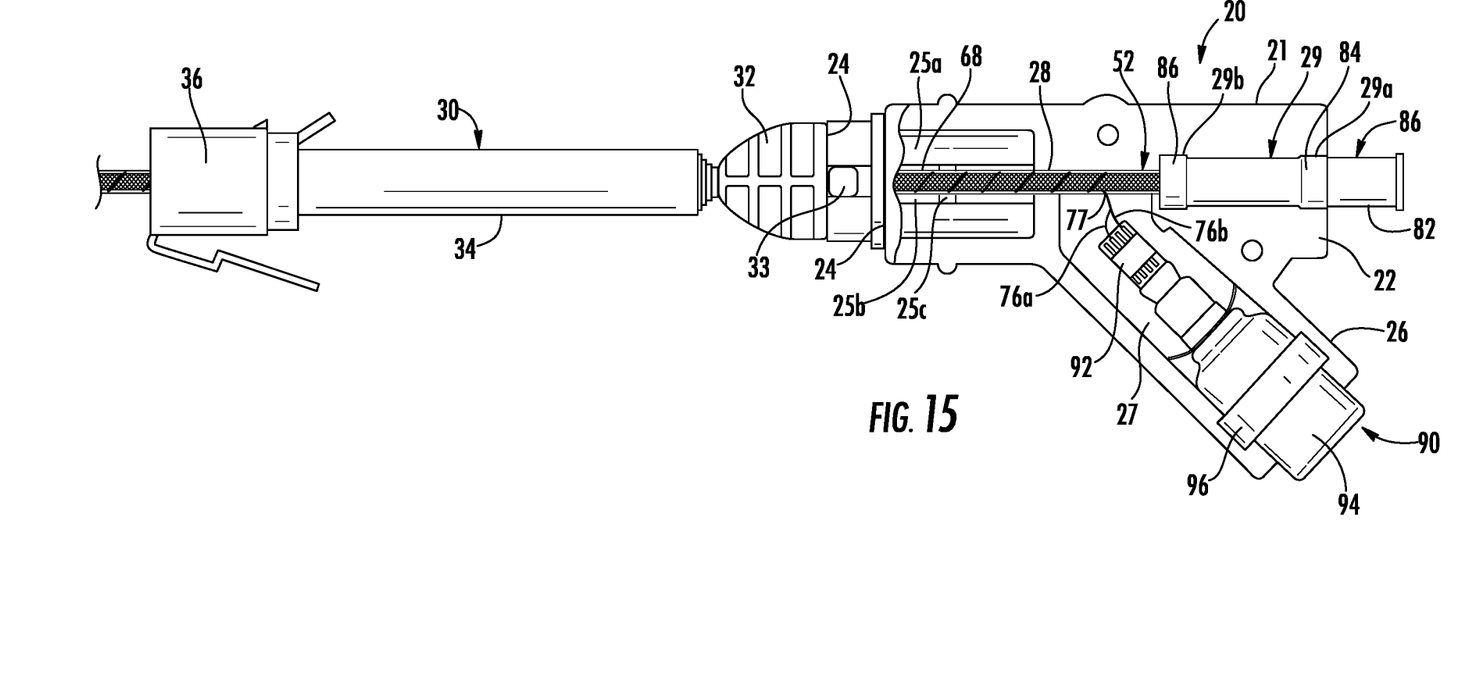
FIG. 15 is a side view of the catheter assembly of FIG. 1 with the half-shell of the body removed.

With particular reference to FIG. 15, the distal end 24 of the body 21 defines an opening 25a configured to receive the first end 32 of the telescopic channel 30. The body 21 may define a slot 25b parallel to the catheter passage 28 and in communication with the opening 25a to receive a clip 33 of the first end 32 of the telescopic channel 30 to rotatably fix the first end 32 of the telescopic channel 30 to the body 21. The distal end 24 of the body 21 may also include a ring 25c positioned about an outer surface of the body 21 transverse to the longitudinal axis of the catheter passage 28 and over the slot 25b. The clip 33 of the first end 32 of the telescopic channel 30 may engage the ring 25c when the clip 33 is disposed within the slot 25b to longitudinally the first end 32 of the telescopic channel 30 to the body 21 of the handle 20. The telescopic channel 30 may be attached a bronchoscope (not shown) and the catheter 50 of the catheter assembly 10 may be inserted through the first end 32 of the telescopic channel 30 until the distal end 24 of the handle 20 receives the first end 32 of the telescopic channel 30.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A catheter system, comprising:
   an elongated body having a proximal end portion and a distal end portion and defining a working channel therethrough;
   a handle operably coupled to the proximal end portion of the elongated body, the handle defining a slot and including a ring coupled to an outer surface of the handle;
   a sensor including a wrapped portion disposed at the distal end portion of the elongated body and adjacent to a distal end of the elongated body and a lead portion extending proximally from the wrapped portion to the handle to electrically couple the lead portion to the handle; and
   a telescopic channel including a clip configured to slide along the slot defined by the handle and engage the ring to removably couple a proximal portion of the telescopic channel to a distal portion of the handle.

2. The catheter system according to claim 1, wherein the sensor is formed of a continuous monolithic wire.

3. The catheter system according to claim 1, wherein the handle includes a proximal guide portion operably coupled to the proximal end portion of the elongated body, the proximal guide portion defining a channel aligned with the working channel of the elongated body for receiving a surgical instrument therethrough.

4. The catheter system according to claim 1, wherein the wrapped portion includes first and second layer of wraps.

5. The catheter system according to claim 1, wherein the sensor is formed of a wire and the lead portion is formed from a twisted pair of leads of the wire.

6. The catheter system according to claim 1, wherein the elongated body defines helical channels about the working channel, the lead portion of the sensor disposed within a helical channel of the elongated body from the distal end portion to the handle.

7. The catheter system according to claim 6, further comprising a braid formed of cords that define the working channel, the helical channels defined between adjacent cords of the braid.

8. The catheter system according to claim 1, wherein the elongated body includes an outer coating disposed over the wrapped portion and the lead portion, the outer coating configured to isolate the working channel from an environment surrounding the elongated body.

9. A catheter system, comprising:
a flexible catheter including:
an elongated body having a proximal end portion and a distal end portion and defining a working channel therethrough; and
a sensor configured to sense a position of a distal end of the elongated body within an anatomy of a patient, the sensor being formed from a wrapped portion of a wire disposed around the distal end portion of the elongated body, the wire including a twisted pair of leads proximal to the wrapped portion and extending to the proximal end portion of the elongated body;
a handle disposed over the proximal end portion of the elongated body and longitudinally and rotatably fixed to the flexible catheter, the handle including an adapter in electrical communication with the sensor, the handle defining a slot and including a ring coupled to an outer surface of the handle; and
a telescopic channel disposed over a portion of the elongated body and including a clip configured to slide along the slot defined by the handle and engage the ring to removably couple a proximal portion of the telescopic channel to a distal portion of the handle.

10. The catheter system according to claim 9, wherein the sensor is formed of a continuous monolithic wire.

11. The catheter system according to claim 9, wherein the wrapped portion of the wire includes a first layer of wraps and a second layer of wraps about the distal end portion of the elongated body.

12. The catheter system according to claim 9, wherein the elongated body defines helical channels about the working channel, the twisted pair of leads of the sensor disposed within a helical channel of the elongated body from the distal end portion to the handle.

13. The catheter system according to claim 12, further comprising a braid formed of cords that define the working channel, the helical channels defined between adjacent cords of the braid.

14. The catheter system according to claim 9, wherein the elongated body includes an outer coating configured to isolate the working channel from an environment surrounding the elongated body.

15. The catheter system according to claim 9, wherein the slot defined by the handle is configured to receive the clip of the telescopic channel such that the telescopic channel is rotatably fixed to the handle when the clip is received in the slot.

16. A flexible catheter, comprising:
an elongated body having a proximal end portion and a distal end portion and defining a working channel therethrough;
a sensor disposed in the distal end portion of the elongated body for detecting the position of a distal end of the elongated body within an anatomy of a patient, the sensor operably coupled to a wire including a twisted pair of leads proximal to the sensor and extending to the proximal end portion of the elongated body;
a handle operably coupled to the proximal end portion of the elongated body, the handle defining a slot and including a ring coupled to an outer surface of the handle; and
a telescopic channel including a clip configured to slide along the slot defined by the handle and engage the ring to removably couple the telescopic channel to the handle.

17. The flexible catheter according to claim 16, wherein an outer coating is disposed over the working channel for isolating the working channel from an environment surrounding the flexible catheter.

18. The flexible catheter according to claim 16, wherein the handle includes a proximal guide portion operably coupled to the proximal end portion of the elongated body, the proximal guide portion defining a channel aligned with the working channel of the elongated body for receiving a surgical instrument therethrough.

19. The flexible catheter according to claim 16, wherein the slot defined by the handle is configured to receive the clip of the telescopic channel such that the telescopic channel is rotatably fixed to the handle when the clip is received in the slot.

20. The flexible catheter according to claim 16, wherein the sensor is formed by a wrapped portion of the wire.

* * * * *